(12) United States Patent
Heimbrock

(10) Patent No.: US 11,592,161 B2
(45) Date of Patent: Feb. 28, 2023

(54) POSITIONABLE PROJECTIONS FOR A PATIENT SUPPORT APPARATUS

(71) Applicant: Hill-Rom Services, Inc., Batesville, IN (US)

(72) Inventor: Richard Henry Heimbrock, Cincinnati, OH (US)

(73) Assignee: Hill-Rom Services, Inc., Batesville, IN (US)

( * ) Notice: Subject to any disclaimer, the term of this patent is extended or adjusted under 35 U.S.C. 154(b) by 379 days.

(21) Appl. No.: 16/907,645

(22) Filed: Jun. 22, 2020

(65) Prior Publication Data

US 2020/0408386 A1    Dec. 31, 2020

Related U.S. Application Data

(60) Provisional application No. 62/866,844, filed on Jun. 26, 2019.

(51) Int. Cl.

| | | |
|---|---|---|
| *A61G 1/04* | (2006.01) | |
| *A61G 7/05* | (2006.01) | |
| *G03B 21/00* | (2006.01) | |
| *F21V 11/08* | (2006.01) | |
| *F21V 14/08* | (2006.01) | |
| *A61B 90/00* | (2016.01) | |

(52) U.S. Cl.
CPC ............... *F21V 11/08* (2013.01); *A61G 1/04* (2013.01); *A61G 7/05* (2013.01); *F21V 14/08* (2013.01); *A61B 90/36* (2016.02); *A61G 2203/20* (2013.01)

(58) Field of Classification Search
CPC ........... A61G 1/04; A61B 90/36; F21V 11/09; F21V 14/08
See application file for complete search history.

(56) References Cited

U.S. PATENT DOCUMENTS

| | | | |
|---|---|---|---|
| 8,607,388 B1 | 12/2013 | Flanagan et al. | |
| 2014/0204347 A1* | 7/2014 | Murphy | G03B 21/2033 |
| | | | 353/57 |
| 2018/0084921 A1* | 3/2018 | Huang | G03B 21/64 |
| 2018/0184984 A1 | 7/2018 | Zerhusen et al. | |

FOREIGN PATENT DOCUMENTS

| | | | | |
|---|---|---|---|---|
| EP | 2777670 A1 | | 9/2014 | |
| EP | 2918255 A1 | | 9/2015 | |
| JP | S63149971 A | | 6/1988 | |
| KR | 20180105352 | * | 9/2018 | ............. A47C 21/00 |
| WO | WO-2017213414 A1 | * | 12/2017 | ............. A47C 19/02 |

* cited by examiner

*Primary Examiner* — David R Hare
*Assistant Examiner* — Adam C Ortiz
(74) *Attorney, Agent, or Firm* — Price Heneveld LLP

(57) ABSTRACT

A patient support apparatus includes a support frame. A projection housing may be rotatably coupled with the support frame. The projection housing may include a body defining an aperture. A light source is configured to emit a beam of light. A projector may be configured to direct the beam of light through the aperture in the body and onto a surface.

17 Claims, 3 Drawing Sheets

POSITIONABLE PROJECTIONS FOR A PATIENT SUPPORT APPARATUS

CROSS-REFERENCE TO RELATED APPLICATION

This application claims priority to and the benefit under 35 U.S.C. § 119(e) of U.S. Provisional Application No. 62/866,844, filed on Jun. 26, 2019, entitled "POSITIONABLE PROJECTIONS FOR A PATIENT SUPPORT APPARATUS," the disclosure of which is hereby incorporated herein by reference in its entirety.

FIELD OF THE DISCLOSURE

The present disclosure generally relates to positionable image projections for a patient support apparatus, and more specifically to a rotatable projection housing for positioning projections for a patient support apparatus.

SUMMARY OF THE DISCLOSURE

According to one aspect of the present disclosure, a patient support apparatus includes a support frame. A projection housing is rotatably coupled with the support frame. The projection housing includes a body defining an aperture. A light source is configured to emit a beam of light. A projector is configured to direct the beam of light through the aperture in the body and onto a surface.

According to another aspect of the present disclosure, a patient support apparatus includes a support frame. A projection housing is rotatably coupled to the support frame. The projection housing includes a projector configured to project an image from the support frame. An angle of projection of the image is adjusted by rotation of the projection housing.

According to yet another aspect of the present disclosure, a patient support apparatus includes a head end and a foot end. A support frame is coupled to one of the head and food end. A projection housing is disposed within and rotatably coupled to the support frame. The projection housing includes a body which defines a first aperture and a second aperture. A first light source is configured to emit a first beam of light. A second light source is configured to emit a second beam of light. A first projector is configured to direct the first beam of light through the first aperture in the body. A second projector is configured to direct the second beam of light through the second aperture in the body, wherein upon alignment with the first and second apertures the first and second projectors are configured to project a first image and a second image, respectively, onto a surface.

According to one aspect of the present disclosure, a patient support apparatus includes a head end and a foot end. The foot end includes a support frame and a projection housing. The projection housing is disposed within and rotatably coupled to the support frame. The projection housing includes a projector configured to project an image through the support frame. An angle of projection of the image is adjusted by rotation of the projection housing.

These and other features, advantages, and objects of the present invention will be further understood and appreciated by those skilled in the art by reference to the following specification, claims, and appended drawings.

DETAILED DESCRIPTION

Figure 1:
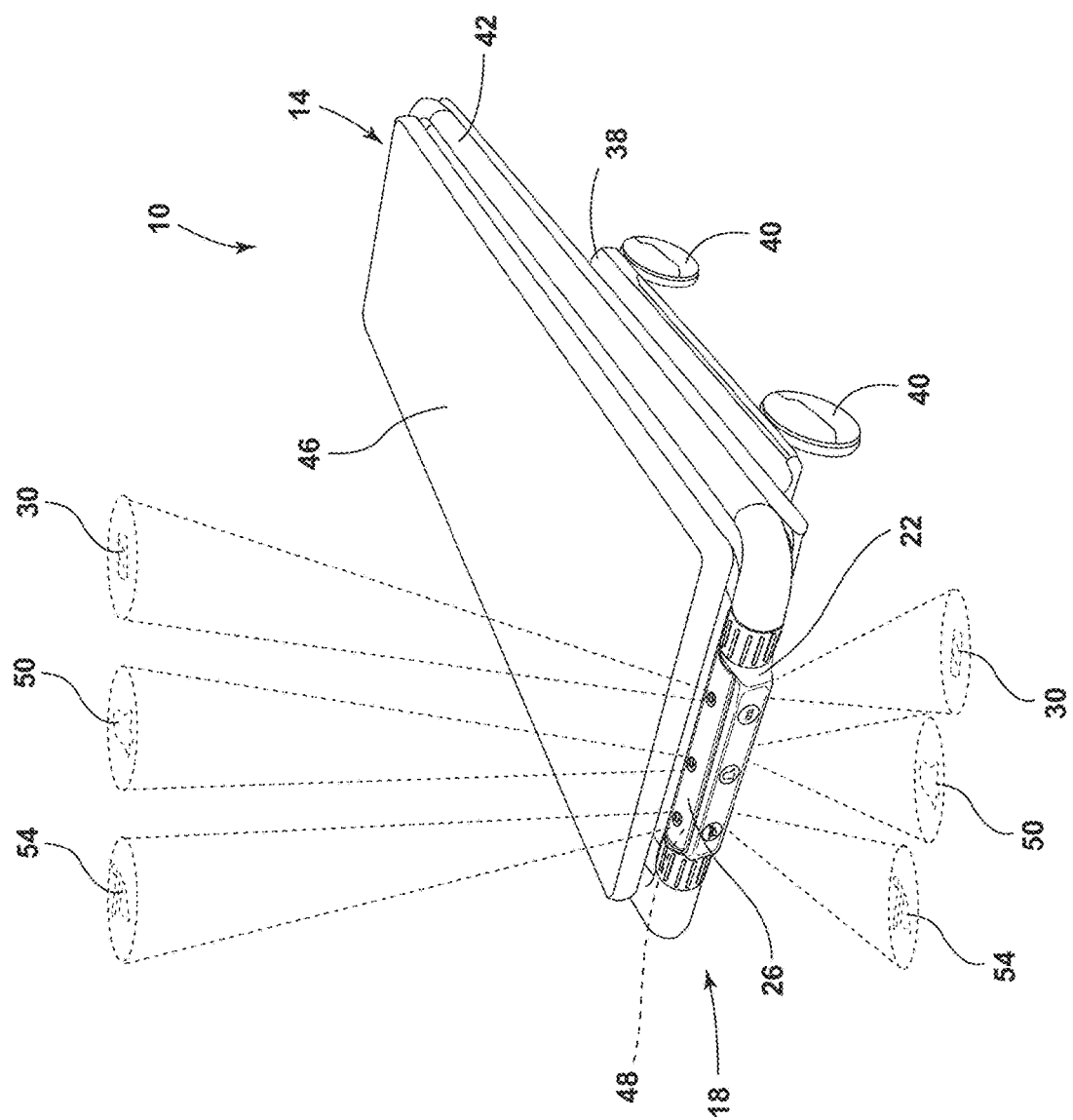
FIG. 1 is a perspective view of a patient support apparatus, according to various aspects described herein.

The present illustrated embodiments reside primarily in combinations of method steps and apparatus components related to positionable image projections for a patient support apparatus. Accordingly, the apparatus components and method steps have been represented, where appropriate, by conventional symbols in the drawings, showing only those specific details that are pertinent to understanding the embodiments of the present disclosure so as not to obscure the disclosure with details that will be readily apparent to those of ordinary skill in the art having the benefit of the description herein. Further, like numerals in the description and drawings represent like elements.

For purposes of description herein, the terms "upper," "lower," "right," "left," "rear," "front," "vertical," "horizontal," and derivatives thereof shall relate to the disclosure as oriented in FIG. 1. Unless stated otherwise, the term "front" shall refer to a surface of the device closest to an intended viewer, and the term "rear" shall refer to a surface of the device furthest from the intended viewer. However, it is to be understood that the disclosure may assume various alternative orientations, except where expressly specified to the contrary. It is also to be understood that the specific devices and processes illustrated in the attached drawings, and described in the following specification are simply exemplary embodiments of the inventive concepts defined in the appended claims. Hence, specific dimensions and other physical characteristics relating to the embodiments disclosed herein are not to be considered as limiting, unless the claims expressly state otherwise.

The terms "including," "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element preceded by "comprises a . . . " does not, without more constraints, preclude the existence of additional identical elements in the process, method, article, or apparatus that comprises the element.

Referring to FIGS. 1-4, reference numeral 10 generally designates a patient support apparatus, which may be in the form of a stretcher. The patient support apparatus 10 may include a head end 14 and a foot end 18. The foot end 18 may include a support frame 22 and a projection housing 26. The projection housing 26 is rotatably coupled to the support frame 22. The projection housing 26 includes a projector configured to project an image 30 from the support frame 22. An angle of projection 34 of the image 30 is adjusted by rotation of the projection housing 26.

Referring now to FIG. 1, the patient support apparatus 10 may include a stretcher. While described as the patient support apparatus 10, it is within the scope of the disclosure that the patient support apparatus 10 may include a hospital bed, a bed frame, a mattress, or any suitable structure for supporting a patient, including, but not limited to: other types of beds, surgical tables, examination tables, and the like.

The illustrated patient support apparatus 10 of FIG. 1 includes a frame 38, which may be in the form of a base frame supported on casters or wheels 40. The base frame 38 is configured to support an upper frame 42. The upper frame 42 may be operable between raised, lowered, and tilted positions relative to the base frame 38. The patient support apparatus 10 may include a support member, such as a mattress 46, disposed on the upper frame 42.

The support frame 22 may be fixed relative to the patient support apparatus 10. In some examples, the support frame 22 extends laterally along the foot end 18 of the patient support apparatus 10 and is integral with, or coupled with the upper frame 42. In some examples, the support frame 22 may be fixedly attached to the upper frame 42. The support frame 22 may retain the rotatable projection housing 26, which may be in the form of a drum. The projection housing 26 may include at least one light projector 48 disposed inside the projection housing 26 and configured to project at least one image, such as the image 30. The projection housing 26 may include multiple light projectors. For example, in FIG. 1, three light projectors are disposed in the projection housing 26 and are configured to project a first image 30, a second image 50, and a third image 54. The images, 30, 50, and 54 may be in the form of a light presentation visible on a surface for indicating conditions or statuses of a function of the patient support apparatus 10, which may include, but are not limited to: a level of charge of a battery, a status of an incontinence detection system, a current head angle, an alert condition, an operating condition of the mattress 46, a bed exit alarm, an indication of whether or not the patient support apparatus 10 is in its lowest position, an indication of whether or not side rails are in a raised position, etc.

Figure 2:
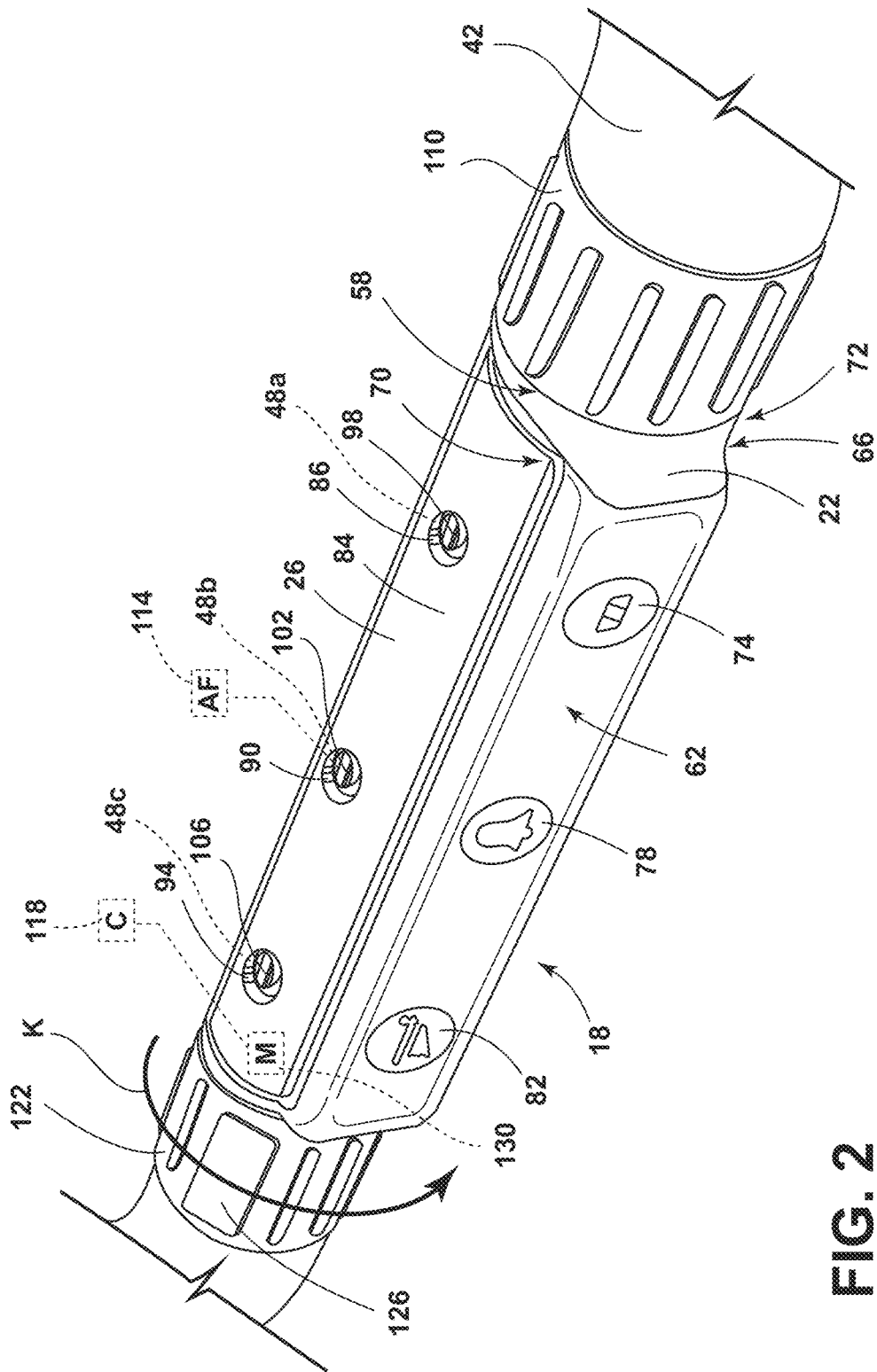
FIG. 2 is an enlarged perspective view of a foot end of the patient support apparatus of FIG. 1.

FIG. 2 illustrates an enlarged view of the foot end 18 of the patient support apparatus 10. The support frame 22 may include an upper portion 58, a middle portion 62 and a lower portion 66. The support frame 22 may be constructed such that at least a portion of the projection housing 26 is visible at the upper portion 58 and the lower portion 66. In this way, the projection housing 26 may not be completely concealed by the support frame 22. For example, the support frame 22 may define a first, or upper, aperture 70 and a second, or lower, aperture 72. The middle portion 62 may include at least one indicator 74, which may include a light source, such as a light emitting diode (LED), configured to selectively illuminate and graphically display conditions or statuses of functions of the patient support apparatus 10. In some examples, three indicators 74, 78, and 82 correspond to the images 30, 50, and 54, respectively.

Figure 3:
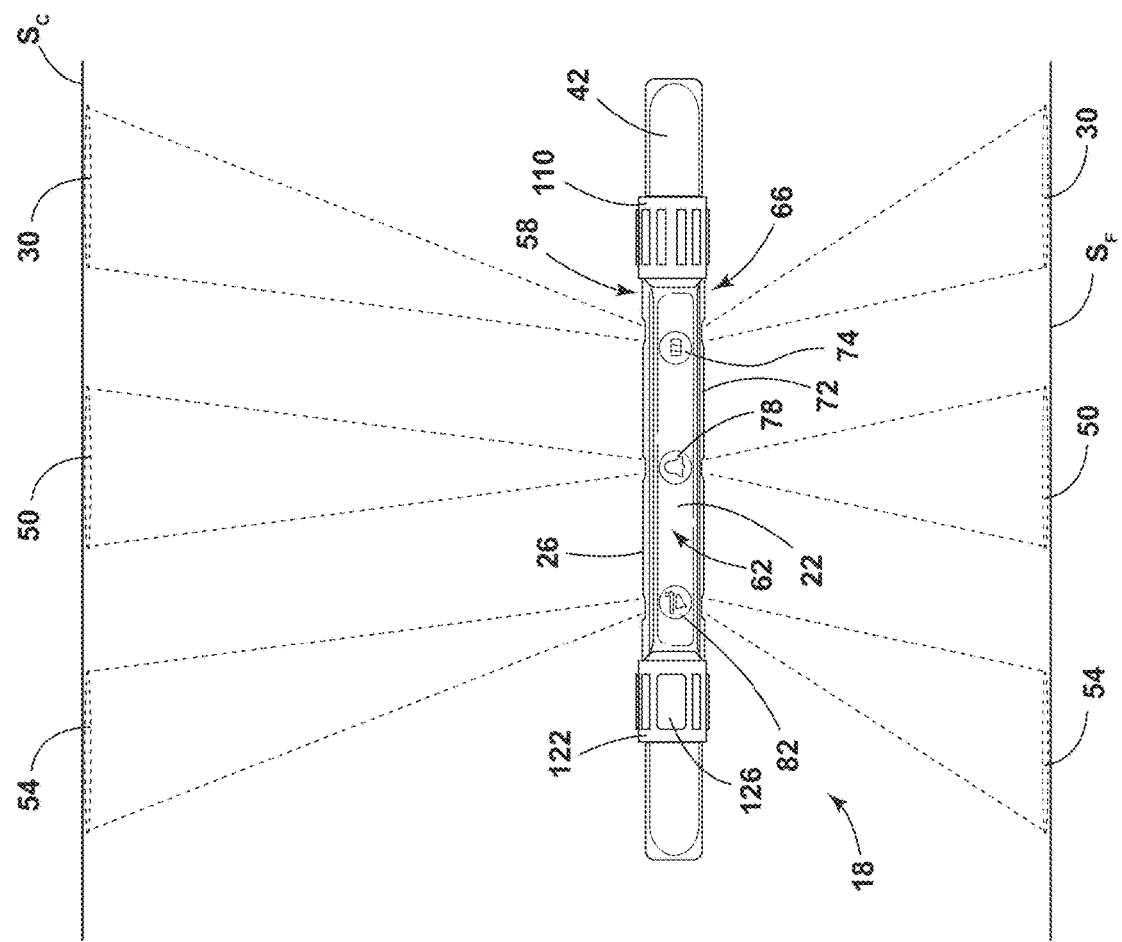
FIG. 3 is an elevation view of the foot end of FIG. 2.

The projection housing 26 may be disposed within the support frame 22. Further, the projection housing 26 includes a body 84 defining at least one aperture, which may include apertures 86, 90 and 94. The at least one light projector 48 may include three light projectors 48a, 48b, and 48c disposed within the projection housing 26. The light projectors 48a, 48b, and 48c are configured to direct beams of light through the apertures 86, 90 and 94 in the body 84 and onto a surface, S (FIG. 3). Accordingly, the light projectors 48a, 48b, and 48c may be aligned with the apertures 86, 90 and 94 to project the images 30, 50, and 54, respectively, through the projection housing 26 and the support frame 22. The apertures 86, 90 and 94, and therefore the light projectors 48a, 48b, and 48c and the images 30, 50, and 54 may be in lateral alignment with the indicators 74, 78, and 82. In this way, a condition or status may be viewed from a plurality of locations.

Lenses 98, 102 and 106 may be provided adjacent the apertures 86, 90 and 94 and may be in alignment with the light projectors 48a, 48b, and 48c such that light emitted through the light projectors 48a, 48b, and 48c may pass through the lenses 98, 102, and 106, respectively. The lenses 98, 102 and 106 may adjust the focus of the images 30, 50, and 54, respectively, on a focal point of the surface S (FIG. 3) by concentrating or dispersing light rays from a light beam. The lenses 98, 102 and 106 may be in any suitable configuration such as a single piece or a compound lens. A focus ring 110 may be operably coupled with the lenses 98, 102 and 106 in order to shift the lenses 98, 102 and 106 for adjusting the focal distance of the images 30, 50, and 54, which may include manually rotating the focus ring 110. Adjusting the focal distance of the images 30, 50, and 54 may adjust the clarity of the images 30, 50, and 54 on the surface, S. The focus ring 110 may be coupled with the support frame 22. However, it is within the scope of various aspects described herein for the focus ring 110 to be coupled with any suitable component of the patient support apparatus 10, which may include the upper frame 42. Alternatively, the lenses 98, 102 and 106 may be shifted automatically by an autofocus optical system 114, which may include one or more sensors, a controller, and a motor. In some examples, the autofocus optical system 114 may be disposed inside the projection housing 26.

The projection housing 26 may include at least one light source adjacent each light projector 48a, 48b, 48c configured to emit or provide a beam of light for generating the images 30, 50, and 54. In this way, the projection housing 26 body 84 may define a first aperture and a second aperture and include a first light source configured to emit a first beam of light and a second light source configured to emit a second beam of light where first and second projectors direct the first and second beams of light through corresponding first and second apertures. In some examples, an amber LED and a green LED may be disposed on a circuit board adjacent each light projector 48. Additionally, a slide may be positioned adjacent each light projector 48, which may include a position aligned between the projector 48a, 48b, 48c and the corresponding aperture 86, 90 and 94. The slides may define a graphic configured to generate the images 30, 50, and 54. For example, the slides may be in the form of a graphic overlay. In this way, illumination of a green LED may be emitted through the light projector 48 and then through the slide and the lens 98 to present the image 30 in green. A controller 118 of the patient support apparatus 10 may be configured to selectively illuminate the light source(s).

Furthermore, the controller 118 may signal the light source (s) to rapidly turn off and on. Thus, the light projector 48 may selectively project the image 30 in a flashing manner to generate a flashing projection. It is also within the scope of the disclosure to adjust the focus of the images 30, 50, and 54 by moving the position of the LEDs closer or further from the apertures 86, 90 and 94. For example, the focus ring 110 may be operably coupled with the LEDs and the circuit board.

The projection housing 26 may be configured to spin, or rotate to adjust the position of the apertures 86, 90 and 94. A knob 122 may be operably coupled with the projection housing 26 for manual rotation of the projection housing 26 relative to the support frame 22, as illustrated by arrow K. While illustrated as moving away from the patient support apparatus 10, the knob 122 and/or projection housing 26 may rotate towards the patient support apparatus 10, or bi-directionally. Additionally, a release lock, which may be in the form of a button 126, may be provided to selectively control rotation of the projection housing 26. The button 126 may be coupled with the knob 122 such that pushing the button 126 releases a locking mechanism and allows for rotation of the projection housing 26. While illustrated as a button 126, the release lock may be in the form of any suitable lock for securing and releasing the projection housing 26 for rotation. In this way, the images 30, 50, and 54 may be locked into position. Alternatively, the projection housing 26 may automatically rotate when commanded by the controller 118 of the patient support apparatus 10. In some examples, an electric motor 130 in communication with the controller 118 may be operably coupled to the projection housing 26 to control the electric motor 130 to automatically rotate the projection housing 26. A user may provide input to the controller 118 for commanding the rotation of the projection housing 26, which may include a position of the projection housing 26. Input can be provided to the controller 118 via any suitable technique, such as touch input to a graphical user interface on a remote or local device. In some examples, rotation of the knob 122 may activate the light sources for projection of the images 30, 50, and 54. Optionally, locking the projection housing 26 into position via the button 126 may activate the light sources. The light sources may be configured to remain activated until the projection housing 26 is rotated into an off position. The off position may include the apertures 86, 90 and 94 being substantially aligned with the middle portion 62 of the support frame 22 such that the apertures 86, 90 and 94 are concealed by the support frame 22. It is within the scope of the disclosure for the controller 118 to activate and deactivate the light sources in a variety of ways including, but not limited to: timing out after a predetermined amount of time, which may be a period of 24 hours or more, in response to audible commands, in response to input from a remote device, a capacitive touch input provided by user, in response to signals from a motion sensor, an ambient light sensor, a proximity sensor, and the like. In some examples, the light source(s) may remain activated as a default condition until the controller detects a deactivation signal.

Referring now to FIG. 3, an elevation view of the foot end 18 is illustrated. The beams of light forming the images 30, 50, 54 may be projected onto a plurality of surfaces, including, but not limited to a floor surface $S_F$ and a ceiling surface $S_c$. In some examples, the projection housing 26 may be rotated such that the apertures 86, 90 and 94 are positioned adjacent the upper portion 58 or the lower portion 66 of the support frame 22. Positioning the apertures 86, 90 and 94 adjacent the upper portion 58, or aligning the projectors 48a, 48b, and 48c adjacent the upper aperture 70, may enable the images 30, 50, 54 to be projected onto, or positioned on, the ceiling surface $S_c$. Positioning the apertures 86, 90 and 94 adjacent the lower portion 66, or aligning the projectors 48a, 48b, and 48c adjacent the lower aperture 72, may enable the images 30, 50, 54 to be projected onto, or positioned on, the floor surface $S_F$. It is within the scope of the disclosure for the images 30, 50, 54 to be simultaneously projected onto more than one surface. For example, the projection housing 26 may include an additional set of apertures and/or light projectors for projecting the images 30, 50, 54 in more than one direction. Additionally, the images 30, 50, 54 may differ from surface to surface. In one example, images 30, 50, 54 indicate different information, or conditions/statuses, from the floor surface $S_F$ to the ceiling surface $S_c$. In another example, images 30, 50, 54 displayed on the floor surface $S_F$ may include additional details compared to the images 30, 50, 54 displayed on the ceiling surface $S_c$, which may include an actual battery charge level indicated by numerals in addition to or alternatively to the graphical representation.

Figure 4:
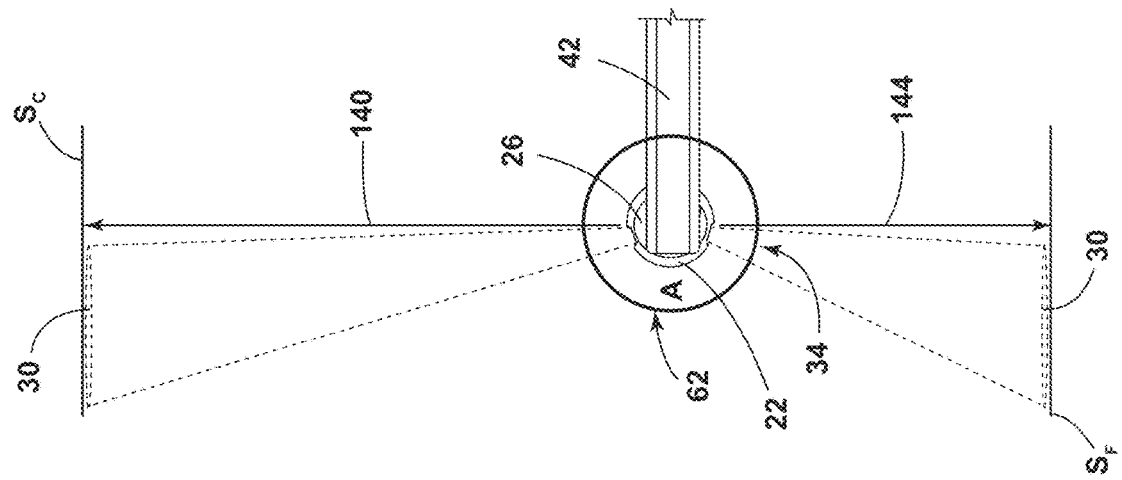
FIG. 4 is a side view of the foot end of FIG. 2.

FIG. 4 is a side view of the foot end 18 illustrating the angle of projection 34 of the image 30. A first vector 140 may represent a 180° position and a second vector 144 may represent a 0° position. The projection housing 26 may be rotatable from 0° to 360° in order to provide for multiple angles of projection 34 as the rotational position of the projection housing 26 relative to the support frame 22 may determine where the images 30, 50, 54 appear. Therefore, rotation of the projection housing 22 adjusts the angle at which the image 30 is projected. In some examples, positioning the apertures 86, 90 and 94 on the projection housing 26 at approximately 180° may position the image 30 onto the ceiling surface $S_c$ and positioning the apertures 86, 90 and 94 at approximately 0° may position the image 30 onto the floor surface $S_F$. It may be desirable to position the image(s) 30, 50, 54 onto a position other than the ceiling or the floor. For example, it may be desirable to position the image(s) 30, 50, 54 on a wall or dividing curtain surface, which may include positioning the apertures 86, 90 and 94 at approximately 135°. As dividing curtains may be located in rooms shared by more than one patient, the dividing curtains provide a private area for an individual patient. The dividing curtains may include a semitransparent material such that the image(s) 30, 50, 54 positioned or projected on an interior surface of the dividing curtain can be transmitted through the curtain material to an exterior surface. Accordingly, the caregiver can view the image(s) 30, 50, 54 on the exterior curtain surface to assess the patient's condition without entering the private area.

Furthermore, in an example where the middle portion 62 of the support frame 22 is positioned at approximately 90°, the images 30, 50, 54 may be prevented from projecting from the end of the foot end 18 by the middle portion 62, which may be due to the projection housing 26 being in the off position (i.e. the apertures 48a, 48b, 48c are concealed by the middle portion 62). Additionally, it is within the scope of the disclosure for the support frame 22 to not include the middle portion 62 such that the angles of projection 34 may include angles of approximately 90°.

According to one aspect of the present disclosure, a patient support apparatus may include a head end and a foot end. The foot end may include a support frame and a projection housing. The projection housing may be disposed within and rotatably coupled to the support frame. The projection housing may include a projector configured to project an image through the support frame. An angle of projection of the image may be adjusted by rotation of the projection housing.

According to another aspect of the present disclosure, the support frame may be stationary.

According to another aspect of the present disclosure, the support frame may include an indicator configured to selectively illuminate.

According to another aspect of the present disclosure, the indicator may correspond to and be in lateral alignment with the image.

According to another aspect of the present disclosure, a knob may be coupled with the projection housing for rotating the projection housing relative to the support frame.

According to another aspect of the present disclosure, the projection housing may include a lens configured to adjust the focus of the image on a surface.

According to another aspect of the present disclosure, the lens may be operably coupled with a focus ring configured to shift the lens.

According to another aspect of the present disclosure, the projection housing may include a light source and a slide, and the projector may be configured to project the light source through the slide to generate the image.

According to another aspect of the present disclosure, the projector may be configured to selectively project the image to generate a flashing projection.

According to another aspect of the present disclosure, a release lock may be configured to selectively control rotation of the projection housing.

According to another aspect of the present disclosure, the support frame further comprises an upper portion and a lower portion.

According to another aspect of the present disclosure, projecting the image adjacent the upper portion may position the image adjacent a ceiling and projecting the image adjacent the lower portion may position the image adjacent a floor.

According to another aspect of the present disclosure, the projection housing is configured to simultaneously project the image on more than one surface.

According to another aspect of the present disclosure, the patient support apparatus may be a stretcher.

For purposes of this disclosure, the term "coupled" (in all of its forms, couple, coupling, coupled, etc.) generally means the joining of two components (electrical or mechanical) directly or indirectly to one another. Such joining may be stationary in nature or movable in nature. Such joining may be achieved with the two components (electrical or mechanical) and any additional intermediate members being integrally formed as a single unitary body with one another or with the two components. Such joining may be permanent in nature or may be removable or releasable in nature unless otherwise stated.

It is also important to note that the construction and arrangement of the elements of the disclosure, as shown in the exemplary embodiments, is illustrative only. Although only a few embodiments of the present innovations have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts, or elements shown as multiple parts may be integrally formed, the operation of the interfaces may be reversed or otherwise varied, the length or width of the structures and/or members or connector or other elements of the system may be varied, the nature or number of adjustment positions provided between the elements may be varied. It should be noted that the elements and/or assemblies of the system may be constructed from any of a wide variety of materials that provide sufficient strength or durability, in any of a wide variety of colors, textures, and combinations. Accordingly, all such modifications are intended to be included within the scope of the present innovations. Other substitutions, modifications, changes, and omissions may be made in the design, operating conditions, and arrangement of the desired and other exemplary embodiments without departing from the spirit of the present innovations.

It will be understood that any described processes or steps within described processes may be combined with other disclosed processes or steps to form structures within the scope of the present disclosure. The exemplary structures and processes disclosed herein are for illustrative purposes and are not to be construed as limiting.

It is also to be understood that variations and modifications can be made on the aforementioned structures and methods without departing from the concepts of the present disclosure, and further it is to be understood that such concepts are intended to be covered by the following claims unless these claims by their language expressly state otherwise.

What is claimed is:

1. A patient support apparatus comprising:
   a support frame, the support frame defining an upper aperture and a lower aperture; and
   a projection housing rotatably coupled with the support frame, the projection housing comprising:
   a body defining an aperture;
   a light source configured to emit a beam of light, wherein the beam of light generates an image indicating one of a condition and status of a function of the patient support apparatus; and
   a projector configured to direct the beam of light through the aperture in the body and onto a surface, wherein aligning the projector adjacent the upper aperture positions the image adjacent a ceiling and aligning the projector adjacent the lower aperture positions the image adjacent a floor.

2. The patient support apparatus of claim 1, wherein rotation of the projection housing adjusts an angle at which the image is projected.

3. The patient support apparatus of claim 1, further comprising:
   a slide defining a graphic, wherein the slide is aligned between the projector and the aperture.

4. A patient support apparatus comprising:
   a support frame, the support frame defining an upper aperture and a lower aperture; and
   a projection housing rotatably coupled to the support frame, the projection housing comprising:
   a projector configured to project the image from the support frame, wherein an angle of projection of the image is adjusted by rotation of the projection housing and aligning the projector adjacent the upper aperture positions an image adjacent a ceiling and aligning a projector adjacent the lower aperture positions the image adjacent a floor, wherein the image indicates one of a condition and status of a function of the patient support apparatus.

5. The patient support apparatus of claim 4, wherein the support frame is fixed relative to the patient support apparatus.

6. The patient support apparatus of claim 4, wherein the support frame comprises an indicator configured to selectively illuminate.

7. The patient support apparatus of claim 6, wherein the indicator corresponds to and is in lateral alignment with the projector.

8. The patient support apparatus of claim 4, further comprising:
   a knob operably coupled with the projection housing for rotation of the projection housing relative to the support frame.

9. The patient support apparatus of claim 4, wherein the projection housing further comprises a lens configured to adjust a focus of the image on a surface.

10. The patient support apparatus of claim 9, wherein the lens is operably coupled with a focus ring configured to shift the lens, thereby adjusting a clarity of the image on the surface.

11. The patient support apparatus of claim 4, wherein the projection housing further comprises:
   a light source configured to provide a beam of light; and
   a slide defining a graphic, wherein the projector is configured to project the beam of light through the slide to generate the image.

12. The patient support apparatus of claim 4, wherein the projector is configured to selectively project the image to generate a flashing projection.

13. The patient support apparatus of claim 4, further comprising:
   a release lock configured to selectively control rotation of the projection housing.

14. The patient support apparatus of claim 4, further comprising:
   an electric motor operably coupled to the projection housing; and
   a controller in communication with the electric motor and configured to control the electric motor to rotate the projection housing.

15. The patient support apparatus of claim 4, wherein the patient support apparatus is a stretcher.

16. A patient support apparatus comprising:
   a head end and a foot end;
   a support frame coupled to one of the head end and foot end; and
   a projection housing disposed within and rotatably coupled to the support frame, the projection housing comprising:
      a body defining a first aperture and a second aperture;
      a first light source configured to emit a first beam of light;
      a second light source configured to emit a second beam of light;
      a first projector configured to direct the first beam of light through the first aperture in the body; and
      a second projector configured to direct the second beam of light through the second aperture in the body, wherein upon alignment with the first and second apertures, the first and second projectors are configured to project a first image and a second image, respectively, onto a surface;
   wherein the first and second images indicate one of a condition and status of a function of the patient support apparatus.

17. The patient support apparatus of claim 16, wherein an angle of projection of the first and second images is adjusted by rotation of the projection housing relative to the support frame.

* * * * *